US012761199B2

(12) United States Patent
Katterbauer et al.

(10) Patent No.: US 12,761,199 B2
(45) Date of Patent: Oct. 13, 2026

(54) LOW-LATENCY WIRELESS COMMUNICATION DEVICE AND PROTOCOL FOR $CO_2$ BOT SENSING COMMUNICATION

(71) Applicant: Saudi Arabian Oil Company, Dhahran (SA)

(72) Inventors: Klemens Katterbauer, Dhahran (SA); Abdullah Awadh Al-Shehri, Dhahran (SA); Ali Abdallah Al-Yousef, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 153 days.

(21) Appl. No.: 18/788,476

(22) Filed: Jul. 30, 2024

(65) Prior Publication Data

US 2026/0036560 A1 Feb. 5, 2026

(51) Int. Cl.

*G01N 33/00* (2006.01)
*H04W 84/18* (2009.01)
*H04W 88/08* (2009.01)

(52) U.S. Cl.

CPC ........... *G01N 33/004* (2013.01); *H04W 84/18* (2013.01); *H04W 88/08* (2013.01)

(58) Field of Classification Search

CPC ..... G01N 33/004; H04W 84/18; H04W 88/08
USPC .......................................................... 340/632
See application file for complete search history.

(56) References Cited

U.S. PATENT DOCUMENTS

| | | | | |
|---|---|---|---|---|
| 8,168,121 | B2 | 5/2012 | Elkins | |
| 8,595,020 | B2 * | 11/2013 | Marino | G06Q 50/00 705/1.1 |
| 9,182,751 | B1 * | 11/2015 | Reeder | G08B 21/182 |
| 12,283,030 | B1 * | 4/2025 | Mishra | G06V 20/52 |
| 2008/0318564 | A1 * | 12/2008 | Kreiner | H04M 3/38 455/420 |
| 2010/0019921 | A1 * | 1/2010 | Kreiner | G08B 25/14 340/4.3 |

(Continued)

FOREIGN PATENT DOCUMENTS

| | | |
|---|---|---|
| CN | 203055141 U | 7/2013 |
| CN | 103106169 B | 8/2015 |

(Continued)

OTHER PUBLICATIONS

Pillai, Parvathy et al.; "Real Time CO2 Monitoring Alert System Based on Wireless Sensor Networks" Intelligent Systems Technologies and Applications 385 (2016); pp. 91-103.

(Continued)

*Primary Examiner* — Omar Casillashernandez
(74) *Attorney, Agent, or Firm* — Bracewell LLP; Constance G. Rhebergen; Brian H. Tompkins

(57) ABSTRACT

A low-latency wireless communication system, devices, and processes for carbon dioxide ($CO_2$) monitoring for a subsurface reservoir. The system includes various wireless $CO_2$ sensing bots that measure $CO_2$ within the reservoir. The $CO_2$ data is wirelessly transferred between the individual $CO_2$ sensing bots and a base station that communicate with the other $CO_2$ sensing bots as peers within a low latency architecture.

14 Claims, 3 Drawing Sheets

(56) References Cited

U.S. PATENT DOCUMENTS

| | | | | |
|---|---|---|---|---|
| 2011/0298598 | A1* | 12/2011 | Rhee | H04W 4/38 340/286.02 |
| 2015/0296024 | A1* | 10/2015 | Snyder | H04W 4/38 340/870.16 |
| 2020/0163286 | A1* | 5/2020 | Wilde | G05B 15/02 |
| 2021/0360070 | A1* | 11/2021 | Cella | G05B 19/042 |
| 2022/0104310 | A1* | 3/2022 | Hu | H04W 84/18 |
| 2022/0107632 | A1* | 4/2022 | Sinha | G06Q 50/06 |
| 2022/0214652 | A1* | 7/2022 | Trikha | H04L 67/51 |
| 2022/0308568 | A1* | 9/2022 | Oh | G05B 23/0221 |
| 2024/0339026 | A1* | 10/2024 | Kelly | G08B 17/12 |
| 2025/0208105 | A1* | 6/2025 | Kubota | G06Q 10/04 |
| 2025/0293968 | A1* | 9/2025 | Guo | H04L 67/10 |

FOREIGN PATENT DOCUMENTS

| | | | |
|---|---|---|---|
| CN | 115884009 | A | 3/2023 |
| CN | 116801211 | A | 9/2023 |
| DE | 202023103484 | U1 | 7/2023 |
| WO | 2011103922 | A1 | 9/2011 |
| WO | 2021102270 | A1 | 5/2021 |
| WO | 2023069776 | A1 | 4/2023 |
| WO | 2024025889 | A1 | 2/2024 |

OTHER PUBLICATIONS

Siddiqi, Murtaza Ahmed et al.; "5G Ultra-Reliable Low-Latency Communication Implementation Challenges and Operational Issues with IoT Devices" Electronics 2019, 8, 981; pp. 1-18.

Thekkath, Chandramohan A. et al.; "Limits to Low-Latency Communication on High-Speed Networks" ACM Transactions on Computer Systems, vol. 11, No. 2, May 1993; pp. 179-203.

* cited by examiner

LOW-LATENCY WIRELESS COMMUNICATION DEVICE AND PROTOCOL FOR $CO_2$ BOT SENSING COMMUNICATION

BACKGROUND

Field of the Disclosure

The present disclosure generally relates to the detection of carbon dioxide ($CO_2$), such as in reservoirs used for carbon dioxide capture and storage (CCS). More specifically, embodiments of the disclosure relate to carbon dioxide ($CO_2$) sensing using low latency wireless communications.

Description of the Related Art

Carbon dioxide ($CO_2$) is present in the atmosphere and produced from a variety of sources. Various operations and industries involve the use, transport, and storage of carbon dioxide ($CO_2$). For example, carbon capture and storage (CCS) may involve the capture and storage of carbon dioxide ($CO_2$) in subsurface reservoirs, including reservoirs previously used in the extraction of oil and gas. The detection of carbon dioxide ($CO_2$) is important in monitoring operations, such as for leak detection. However, some environments present numerous challenges to detecting carbon dioxide ($CO_2$). The subsurface reservoirs used in CCS are particularly challenging with respect to carbon dioxide ($CO_2$) detection, as such reservoirs are often located deep underground and are difficult to access and monitor.

SUMMARY

The detection of carbon dioxide ($CO_2$) in reservoirs and other structures may rely on data transmission over wireless networks. However, achieving both low latency (for example, an end-to-end (E2E) latency of less than 1 ms) and ultra-reliable communications is difficult, and the trade-off between high reliability (for example, greater than 99.9999%) and low latency presents further complications.

The 5G standard for cellular networks provides particular requirements for low-latency and enhances data transmission rates for greater data transmission sizes and multi-party communication. The objective of 5G is to create a single platform to provide a wide range of services that are classified by the International Telecommunication Union (ITU) into three categories: 1) enhanced mobile broadband (eMBB), 2) massive machine type communication (mMTC), and ultra-reliable and low latency communication (URLLC).

The use of 1 millisecond (ms) E2E latency in 5G mobile systems is based on the fact that 4G mobile communications can achieve an E2E latency of 30 to 100 ms. The 4G E2E latency was in turn improved by several hundred milliseconds of the third generation (3G) mobile communications that develop from the second generation (2G). However, low latency capability cannot be satisfied by legacy mobile communication systems because of the limitations of inherent network architecture and communication techniques within the communication systems.

Network latency includes control plane latency and user plan latency. Control plane latency refers to a terminal to switch from idle state to connected state, whereas user plane latency refers to the time for an Internet Protocol (IP) message to be sent from a terminal to the application server and then returned to the terminal. Both latencies have an effect on network latency, but user plane latency may be the larger contributor. In terms of network architecture, user plane latency includes several components, including air interface, bearing network, core network and public data network (PDN)/Internet.

The total unidirectional transmission latency may be determined according to the following:

$$T = \text{T\_Radio} + \text{T\_Bearing} + \text{T\_Core} + \text{T\_PDN} \quad (1)$$

Where T_Radio is the latency from the user terminal to the radio access network (also referred to as the air interface latency), which is mainly affected by the physical layer transmission; T_Bearing is the latency for transmission on the bearing/backhaul network that bears the connection between the radio access network and the core network, and between the core network and the PDN; T_Core is the processing latency inside the core network (the processing may include mobility management, users' IP address allocation, security management, bearer control, etc.); and T_PDN is the latency of content deliver for the PDN to process requests and establish bearers. The E2E latency is thus twice as long as the total unidirectional transmission latency T, that is 2×T.

As the main part of T_Radio, the physical transmission latency may be divided into five distinct components as follows:

$$TPL = \text{T\_que} + \text{T\_ttt} + \text{T\_proc} + \text{T\_prop} + \text{T\_retr} \quad (2)$$

Where T_que is the queuing latency and is the time needed for the current packet to wait for the completion of the transmission of the previous packet. The queuing latency of a particular packet depends on the number of packets arriving in advance and waiting for transmission to the link. If the queue is empty and no other data packets are currently being transmitted, the queuing latency of the data packet is 0. T_ttt is the time-to-transmission latency and is the time required to push all the bits of a data packet to the link (from the first bit of the transmitted data packet to the last bit of the packet). T_proc is the processing latency and includes encoding and decoding, modulation and demodulation, channel interleaving, channel estimation, rate matching, layer mapper, scrambling, data, and control multiplexing, etc. These factors depend not only on physical layer technologies, but also on the processing capacity of user terminals and base stations. T_prop is the propagation latency and is the time it takes for electromagnetic wave to propagate a certain distance in the channel. T_retr is the latency of retransmission. Low link reliability can easily result in packet loss, which then involves retransmitting.

E2E latency is the sum of latency on multi-segment paths. Thus, a latency of 1 ms cannot be satisfied only by optimizing a local latency. However, a network architecture for low-latency also presents several challenges, such as: 1) cost and practicality 2) efficient utilization and management of heterogenous networks while maintaining low latency; 3) implementation of software-defined networks (SDNs) and network function virtualizations (NFVs) that lack unified standards; 4) reservoir management and interference control of unmanned aerial vehicles (UAVs) and satellites that can be integrated into traditional cellular networks; and 5)

designing new bearer networks and protocols to overcome interference and collision in ultra-sense cellular networks.

In view of the above issues and challenges, embodiments of the disclosure are directed to a low-latency wireless communication system, devices, and protocol having carbon dioxide ($CO_2$) sensing device (referred to as "bots").

In one embodiment, a system for monitoring carbon dioxide ($CO_2$) in a subsurface reservoir is provided. The system includes a plurality of $CO_2$ sensing devices, each $CO_2$ sensing device having a $CO_2$ sensor, a radio unit, and a microprocessor, such that each of the plurality of $CO_2$ sensing devices is operable to communicate as a peer over a radio area network. The system also includes a base station having a low latency unit, a plane function entity, and a radio unit, the base station operable to communicate as a peer over the radio area network, such that the low latency unit is operable to receive data from at least one of the plurality of $CO_2$ sensing devices and the plane function data is operable to receive data from the low latency unit. Each of the plurality of $CO_2$ sensing devices is operable to transmit a $CO_2$ measurement to the base station over the radio area network.

In some embodiments, the system includes a local server configured to process the CO2 measurement, such that the plane function entity is operable to transmit the CO2 measurement to the local server after receipt from the low latency unit. In some embodiments, the local server is configured to determine a CO2 flux measurement using the CO2 measurement. In some embodiments, a server configured to communicate with a cloud computing service over a network, such that the plane function entity is operable to transmit the CO2 measurement to the server after receipt from the low latency unit. In some embodiments, the CO2 sensor is a non-dispersive infrared CO2 sensor. In some embodiments, each $CO_2$ sensing device of the plurality of $CO_2$ sensing devices includes a battery.

In another embodiment, a method for monitoring carbon dioxide ($CO_2$) in a subsurface reservoir is provided. The method includes receiving, at a low latency unit of a base station and over a radio area network, a CO2 measurement from a CO2 sensing device disposed in the subsurface reservoir, the CO2 sensing device having a $CO_2$ sensor, a radio unit, and a microprocessor, and the base station having a low latency unit, a plane function entity, and a radio unit, the base station operable to communicate as a peer over the radio area network. The method also includes providing the CO2 measurement from the low latency unit to a plane function entity of the base station and transmitting the CO2 measurement from the plane function entity of the base station to a server.

In some embodiments, the method includes transmitting the CO2 data from the CO2 sensing device disposed in the subsurface reservoir to the base station. In some embodiments, the method includes deploying the CO2 sensing device in the subsurface reservoir via an injection well accessing the subsurface reservoir. In some embodiments, the server is a local server. In some embodiments, the local server is configured to determine a CO2 flux measurement using the CO2 measurement. In some embodiments, the server is configured to communicate with a cloud computing service over a network. In some embodiments, the CO2 sensor is a non-dispersive infrared CO2 sensor. In some embodiments, the CO2 sensor includes a battery.

In another embodiment, a non-transitory computer-readable storage medium having executable code stored thereon for monitoring carbon dioxide ($CO_2$) in a subsurface reservoir is provided. The executable code includes a set of instructions that cause a processor to perform operations that include receiving, at a low latency unit of a base station and over a radio area network, a CO2 measurement from a CO2 sensing device disposed in the subsurface reservoir, the CO2 sensing device having a $CO_2$ sensor, a radio unit, and a microprocessor, and the base station having a low latency unit, a plane function entity, and a radio unit, the base station operable to communicate as a peer over the radio area network. The operations also include providing the CO2 measurement from the low latency unit to a plane function entity of the base station and transmitting the CO2 measurement from the plane function entity of the base station to a server.

In some embodiments, the operations include transmitting the CO2 data from the CO2 sensing device disposed in the subsurface reservoir to the base station. In some embodiments, the operations include deploying the CO2 sensing device in the subsurface reservoir via an injection well accessing the subsurface reservoir. In some embodiments, the server is a local server. In some embodiments, the local server is configured to determine a CO2 flux measurement using the CO2 measurement. In some embodiments, the server is configured to communicate with a cloud computing service over a network. In some embodiments, the CO2 sensor is a non-dispersive infrared CO2 sensor. In some embodiments, the CO2 sensor includes a battery.

DETAILED DESCRIPTION

The present disclosure will be described more fully with reference to the accompanying drawings, which illustrate embodiments of the disclosure. This disclosure may, however, be embodied in many different forms and should not be construed as limited to the illustrated embodiments. Rather, these embodiments are provided so that this disclosure will be thorough and complete, and will fully convey the scope of the disclosure to those skilled in the art.

Embodiments of the disclosure includes a low-latency wireless communication system, devices, and processes for carbon dioxide ($CO_2$) monitoring for subsurface reservoirs. The system includes various wireless $CO_2$ sensing devices (referred to as "bots") that measure $CO_2$ within the reservoir. The $CO_2$ data is wirelessly transferred between the individual $CO_2$ sensing devices and a base station that communicate with the other $CO_2$ sensing devices within a low latency architecture. The CO2 monitoring system described in the disclosure provides real-time CO2 flux monitoring while being modularized and adaptable for various CO2 intervals. Additionally, the system enables low-latency communication between the $CO_2$ sensing devices, base stations, and processing servers.

Figure 1:
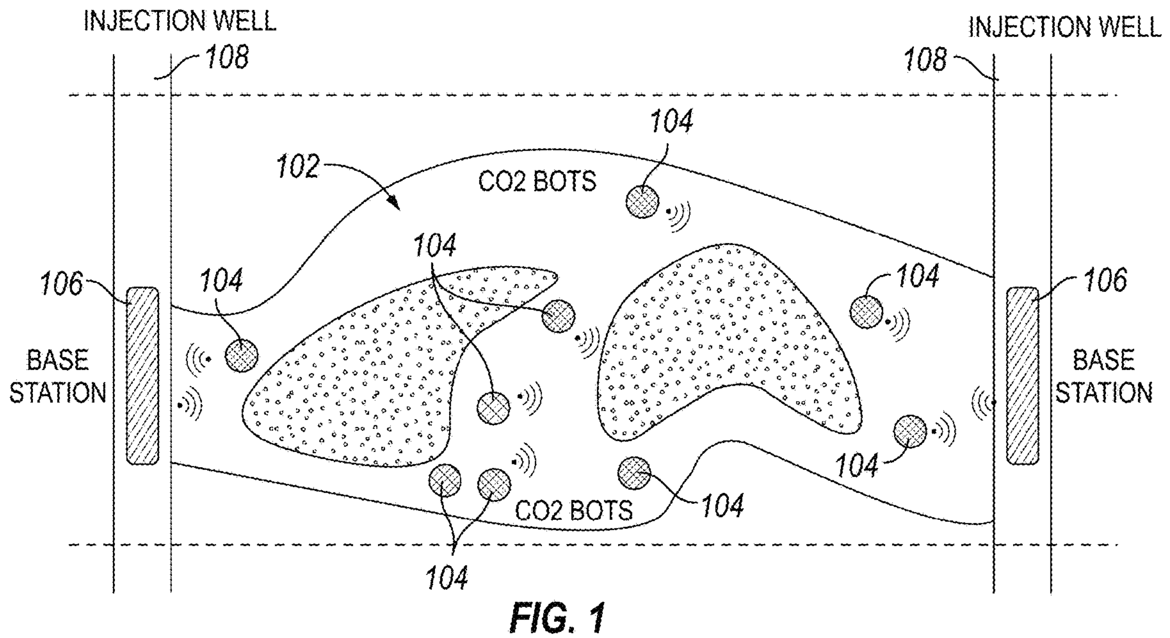
FIG. 1 is a schematic diagram of a $CO_2$ monitoring system for a subsurface reservoir in accordance with an embodiment of the disclosure.

FIG. 1 depicts a $CO_2$ monitoring system 100 for a subsurface reservoir 102 using wireless CO2 sensing bots 104 in accordance with an embodiment of the disclosure. As show in the embodiment depicted in FIG. 1, the CO2 monitoring system 100 may also include low latency CO2 base stations 106 disposed in injection wells 108 used to access the reservoir 102. The reservoir 102 may be used to store CO2 injected into the reservoir 102 via the injection wells, such as in a carbon capture and storage (CCS) operation.

As shown in FIG. 1, multiple $CO_2$ sensing bots 104 may be disposed to monitor $CO_2$ levels in or around the reservoir 102. In some embodiments, the $CO_2$ sensing bots 104 may be disposed in the reservoir 102, outside the reservoir 102, or combination thereof. The number and placement of $CO_2$ sensing bots 104 may be based on the size and shape of the reservoir to be monitored, enabling the system 100 to adapt to different reservoir sizes. The base stations 106 may receive wireless transmissions from the $CO_2$ sensing bots 104 over a radio area network via the low latency wireless communication described in the disclosure. For example, the $CO_2$ sensing bots 104 may transmit $CO_2$ data to the base stations 104. In some embodiments, the base stations 104 may transmit the $CO_2$ data to a local server or to an external server or a cloud computing service for processing.

Figure 2:
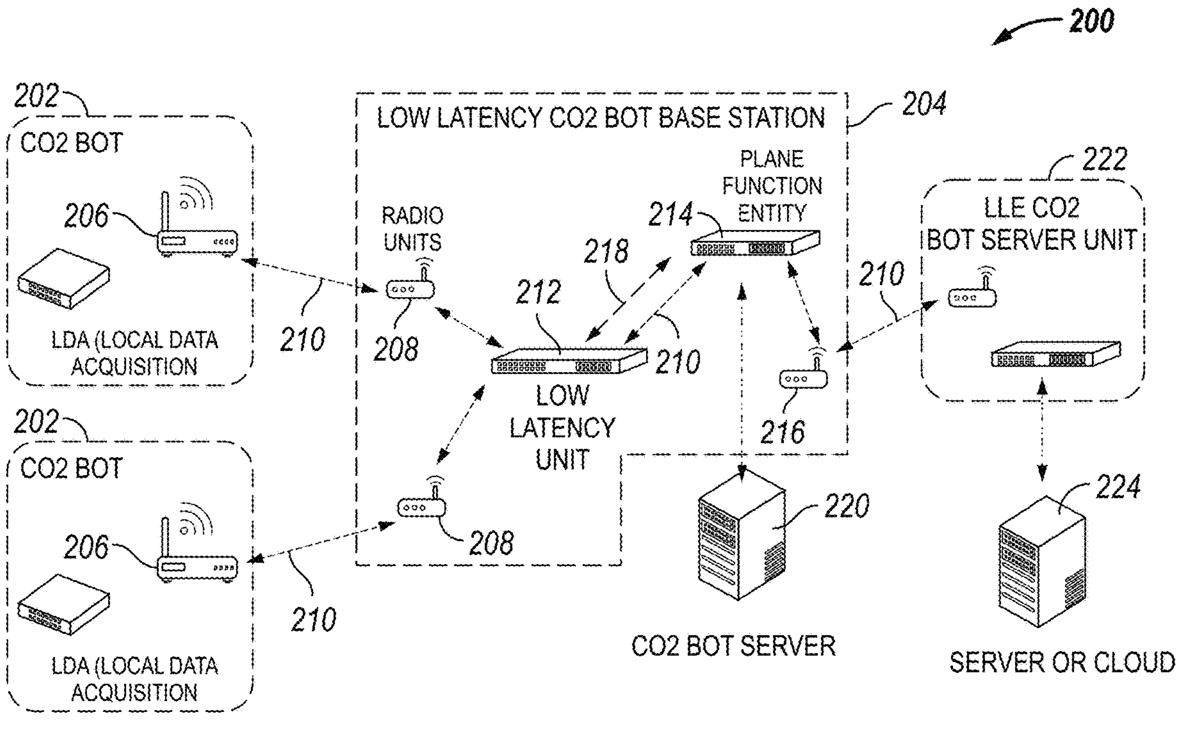
FIG. 2 is a schematic diagram of various components of a $CO_2$ monitoring system for a subsurface reservoir in accordance with an embodiment of the disclosure.

FIG. 2 depict various components of a $CO_2$ monitoring system 200 in further detail in accordance with an embodiment of the disclosure. The $CO_2$ monitoring system 200 includes CO2 sensing bots 202 and a low latency CO2 bot base station 204. The CO2 sensing bots 202 perform local data acquisition (LDA) of CO2 data for transmission to the low latency CO2 bot base station 204. Each CO2 sensing bot 202 may thus include a radio transceiver unit 206 (that is, a wireless transceiver units) for transmission over a radio area network (RAN). The base station 204 may also include radio unit 208 (also referred to as a "wireless unit" or "wireless transceiver" for transmission over the radio area network. Thus, the CO2 sensing bots 202 may wirelessly communicate with the CO2 base station over the radio area network (RAN), providing a low latency local data flow as illustrated by arrows 210.

The low latency CO2 bot base station 204 may also include distributed units 212 and 214 for communication with the CO2 sensing bots 202. In some embodiments, one distributed unit 212 may be a low latency unit that may process communication with the CO2 sensing bots 202 via the wireless radio units 208. In some embodiments, the other distributed unit 214 may process other communication via another radio unit 216 as described below. The distributed units 212 and 214 may communicate with each other as indicated by internal data flow arrow 218. As indicated by arrow 210, such communication is also a low latency local data flow. Each CO2 sensing bot 202 and base station 204 in the $CO_2$ monitoring system 200 behaves as a "peer" in the network, thus enabling peer-to-peer data transmission without the centralization of the communication via a third element.

In some embodiments, the $CO_2$ monitoring system 200 includes or communicates with a $CO_2$ bot server 220 for local processing of data. For example, the low latency CO2 bot base station 204 may communicate with the $CO_2$ bot server 220 over a separate network (not shown). In some embodiments, the $CO_2$ monitoring system 200 includes or communicates with a low latency encryption (LLE) CO2 bot server unit 222 that in turn communicates with an external server or cloud computing service 224 for offsite processing of data. For example, the low latency CO2 bot base station 204 may communicate with the CO2 bot server unit 222 via radio unit 216 over the same or different radio area network (RAN) to establish low latency local data flow (as shown by arrow 210). In some embodiments, the processing by the $CO_2$ bot server 220 or the external server or cloud computing service 224 may include a determination of CO2 flux (that is, a determination of the rate of transfer of CO2 from the reservoir (and, in some instance, surrounding geological structures) to the atmosphere. Such determination may be performed by measuring the change in CO2 concentration over time using the CO2 sensing bots. In some embodiments, the processing may include determine a CO2 flow interval (a time period over which the CO2 flow or flux is measured). Additionally, in some embodiments, the processing may include a determination of CO2 leakage from a reservoir. In such embodiments, a notification, such as alert, may be provided by the $CO_2$ bot server 220 or the external server or cloud computing service 224 if the leakage exceeds a threshold. The leakage may be based on an instantaneous CO2 concentration, an average CO2 concentration over a time period, or a rate of change of CO2 concentration.

The CO2 data exits the CO2 sensing bots 202 encapsulated as a packet inside a tunnel and may be processed by the intermediate devices (for example, peers such as other bots) via recognition of the media access control (MAC) layer encapsulation to arrive at the low latency CO2 bot base station 204. The packets exit the tunnel at the low latency unit 212 that is connected to the other distributed unit 214 having the plane function entity (PFE). The plane function entity (PFE) is the interconnect point between the sensor data network of the CO2 sensing bots 202 and data networks (for example, encapsulation and decapsulation of the General Packet Radio Service (GPRS) Tunneling Protocol) for communication with a server. The packets may then be routed to an application on the local $CO_2$ bot server 220 or to the external server or cloud service 224. In some embodiments, the plane function entity (PFE) may be distributed, allowing a plane function entity (PFE) to serve as an anchor for the overall network while deploying a local PFE onsite to reduce the path to local applications.

In some embodiments, a multiaccess edge computing (MEC) function may be implemented in the CO2 sensing bots and the base station to improve handling of local application services. In such embodiments, tunnels may be terminated at a server that is nearest to the cell radio. In such embodiment, network delays from end-to-end latency may be reduced or eliminated because the network traffic does not traverse back to a central data center or the cloud. In such embodiments, a latency for the CO2 bot sensing application and interpretation may be less than 10 ms.

Figure 3:
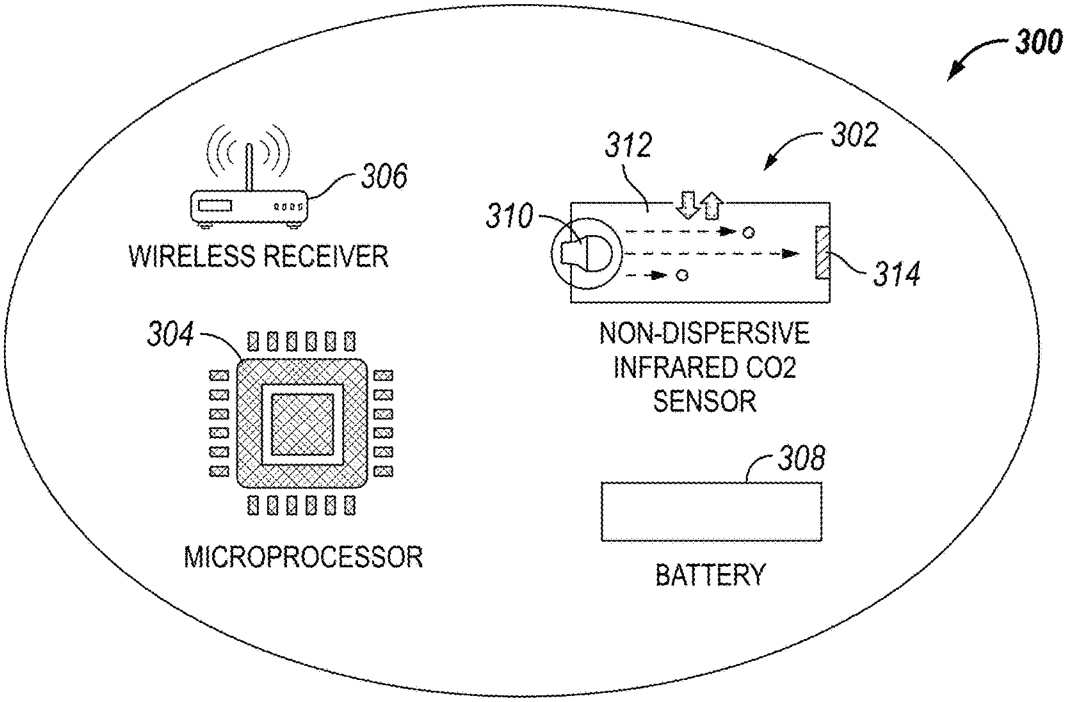
FIG. 3 is a schematic diagram of a CO2 sensing device in accordance with an embodiment of the disclosure.

FIG. 3 depicts a CO2 sensing bot 300 in accordance with an embodiment of the disclosure. The CO2 sensing bot 300 may include a non-dispersive infrared CO2 sensor 302, a microprocessor 304, a radio unit 306, and a battery 308. The non-dispersive infrared CO2 sensor 302 may include a light emitter 310, and optical cavity 312 that receives a gas (that is, a gas having CO2 and potentially other components), and an infrared sensor 314. The light source 302 may emit an infrared light that into the CO2 gas in the optical cavity 312; the remaining infrared light is detected by the infrared sensor which measures the intensity of the light. The microprocessor 304 may receive signals from the non-dispersive infrared CO2 sensor 302 and determine a CO2 measurement (for example, a CO2 value or concentration) by comparing the detected intensity of infrared light to a reference intensity of the light emitter to determine how much light was absorbed by the CO2 in the optical cavity 312. The absorbed light is directly proportional to the CO2 in the gas in the optical cavity 312.

The radio unit 306 may transmit CO2 data to a peer (for example, a base station or another CO2 sensing bot) using the low-latency communication described in the disclosure. The battery 308 may provide power to the various components of the CO2 sensing bot and may be any type of suitable battery for the subsurface environment in which the CO2 sensing bot is deployed. Such battery types may include, for example, nickel cadmium, lithium ion (of any suitable chemistry), and alkaline batteries.

Figure 4:
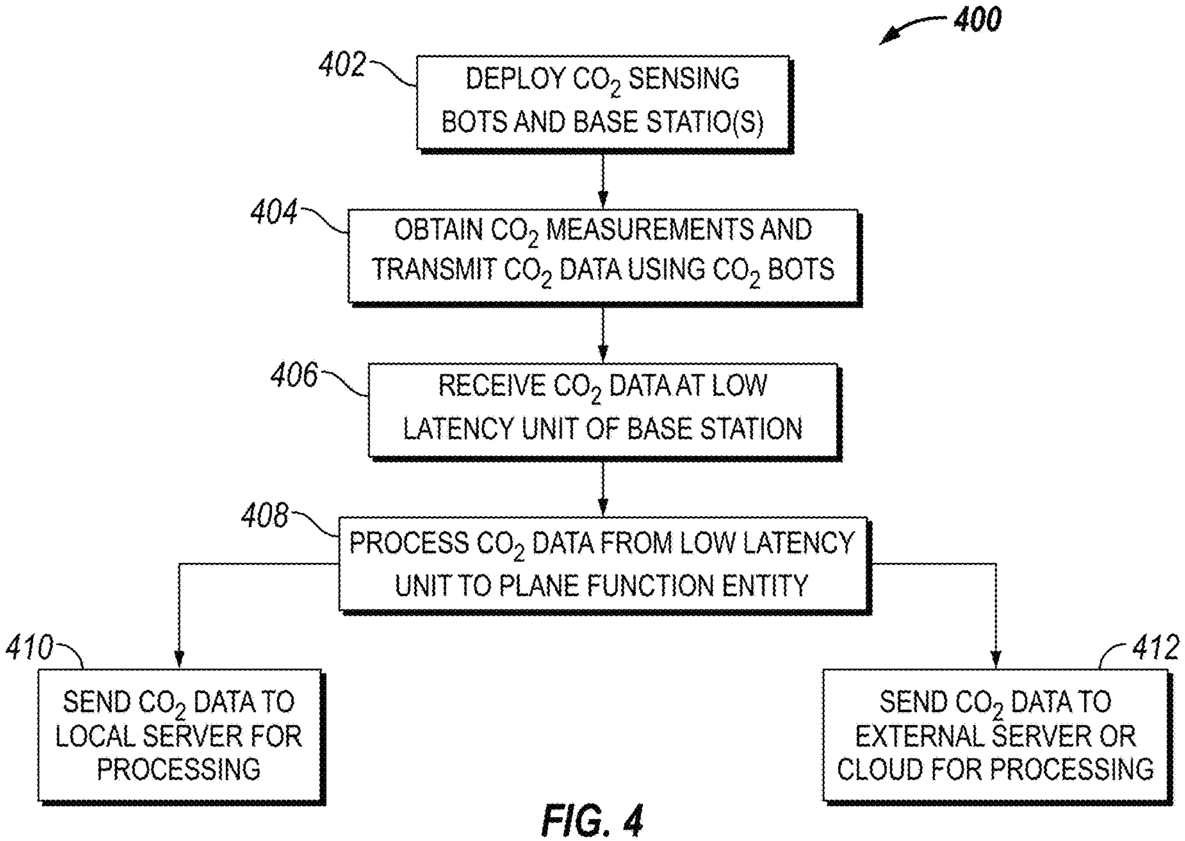
FIG. 4 is a flowchart of a process for monitoring CO2 in a subsurface reservoir in accordance with an embodiment of the disclosure.

FIG. 4 depicts a process 400 for monitoring CO2 according to embodiments of the disclosure. Initially, CO2 sensing bots and one or more base stations may be deployed in a subsurface environment (block 402) to monitor CO2 that may be located in a subsurface reservoir. The CO2 sensing bots may be deployed in a reservoir using one or more injection wells that access the reservoir. Similarly, a CO2 base station may be deployed using the one more injection wells at a position optimal for receiving transmissions from one or more CO2 sensing bots.

The $CO_2$ sensing bots may measure $CO_2$ gas (block 404) and transmit $CO_2$ data (in data packets) via the low latency radio area network. The $CO_2$ data (that is, packets) is then received at a low latency unit at a base station (block 406) and are then processed by a plane function entity (PFE) in the base station (block 408). The plane function entity may then route $CO_2$ data (that is, packets) over a data network to a local server (block 410) or to an external server or cloud system (block 412) for application processing. As discussed in the disclosure, such processing may include a determination of CO2 flux (that is, a determination of the rate of transfer of CO2 from the reservoir (and, in some instance, surrounding geological structures) to the atmosphere. In some embodiments, the processing may include determine a CO2 flow interval (a time period over which the CO2 flow or flux is measured). Additionally, in some embodiments, the processing may include a determination of CO2 leakage from a reservoir. In such embodiments, a notification, such as alert, may be provided if the leakage exceeds a threshold.

Figure 5:
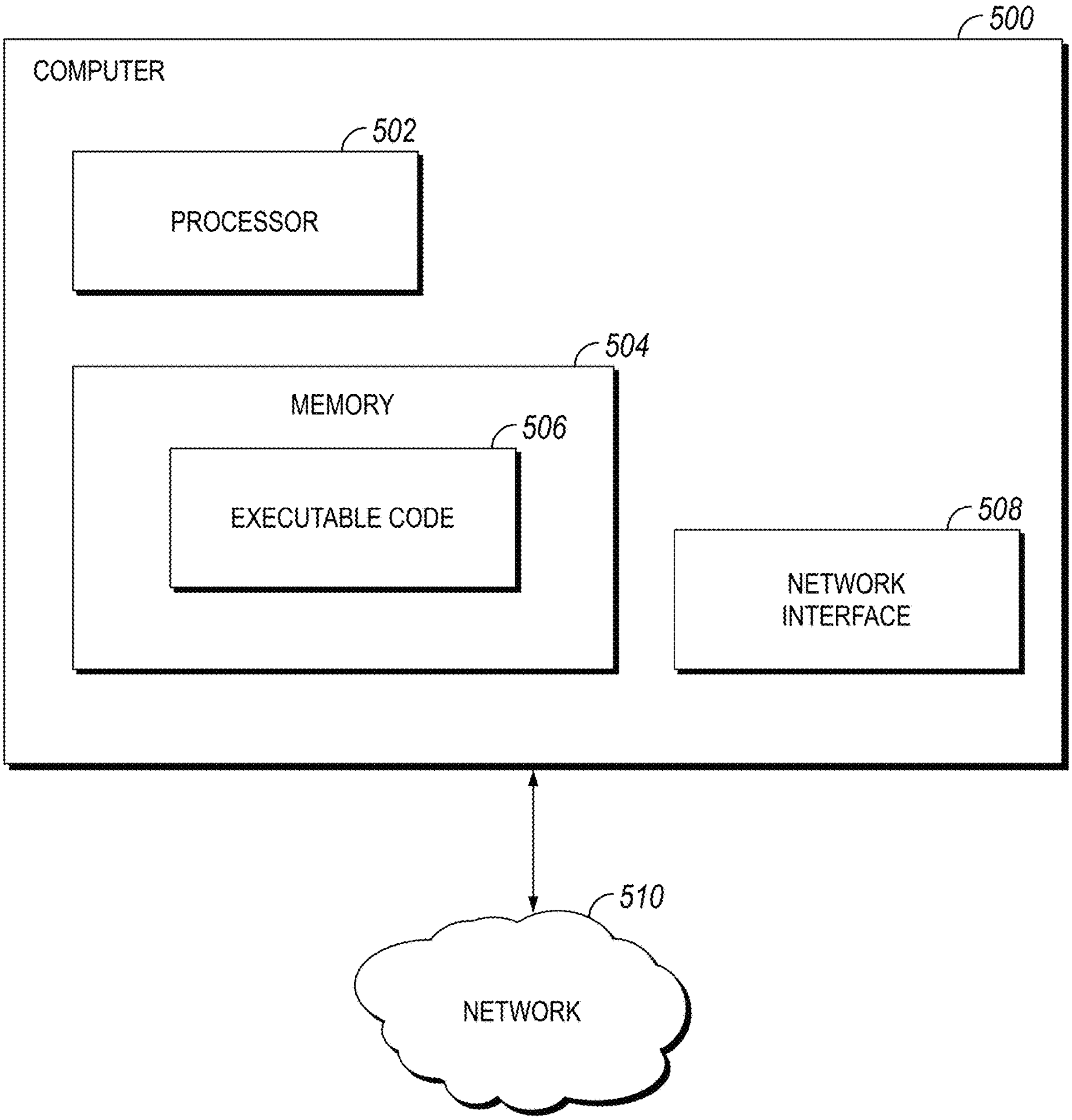
FIG. 5 is a block diagram of a computer in accordance with an embodiment of the disclosure.

FIG. 5 depicts a computer 500 that includes a processor 502 and memory 504 coupled to the processor 502 to store operating instructions in accordance with an embodiment of the disclosure. The computer 500 may be representative of a base station, a bot server, a server unit, or an external server as described in the disclosure. The processor 502 may include one or more processors, and may include "general-purpose" microprocessors and special purpose microprocessors, such as one or more reduced instruction set (RISC) processors, such as those implementing the Advanced RISC Machine (ARM) instruction set. Additionally, the processor 402 may include single-core processors and multicore processors, such as those from Intel Corporation or Advanced Micro Devices (AMD). The computer 500 may in some cases also be a computer of any conventional type of suitable processing capacity, such as a personal computer, laptop computer, or any other suitable processing apparatus. The computer 500 may also be representative of resources available in a computer cluster or a cloud-computing platform. In some embodiments, the computer 500 may include or be connected to a power source (not shown), such as a battery, alternating current (AC) utility power, or other power source.

The computer 500 includes executable code 506 stored in non-transitory memory 504 of the computer 500. The executable code 506 according to the present disclosure is in the form of computer operable instructions causing the data processor 502 to receive input data and provide outputs based on processing the input data. The computer operable instructions of the executable code 506 may thus perform the operations described in the disclosure for processing and transmitting $CO_2$ data, such as those described in FIG. 4.

The executable code 506 may be in the form of microcode, programs, routines, or symbolic computer operable languages capable of providing a specific set of ordered operations controlling the functioning of the computer 500 and direct its operation. The instructions of executable code 506 may be stored in memory 504 of the computer 500, or on computer diskette, magnetic tape, conventional hard disk drive, electronic read-only memory, optical storage device, or other appropriate data storage device having a non-transitory computer readable storage medium stored thereon.

The computer 500 may include a network interface 508 for communication over a network 510 (for example, a local area network (LAN), wide area network (WAN, the Internet, and so on). The network interface 508 may implement a suitable technology for communication with the network 510, such as Ethernet, Wi-Fi, or other technologies. In some embodiments, the network interface 508 may include a radio unit for communication over a radio area network (RAN) as described in the disclosure.

Ranges may be expressed in the disclosure as from about one particular value, to about another particular value, or both. When such a range is expressed, it is to be understood that another embodiment is from the one particular value, to the other particular value, or both, along with all combinations within said range.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used in the disclosure are for organizational purposes only and are not meant to be used to limit the scope of the description.

What is claimed is:

1. A system for monitoring carbon dioxide ($CO_2$) in a subsurface reservoir, comprising:

a plurality of $CO_2$ sensing devices, each $CO_2$ sensing device comprising a $CO_2$ sensor, a radio unit, and a microprocessor, wherein each of the plurality of $CO_2$ sensing devices is operable to communicate as a peer over a radio area network;

a base station comprising a low latency unit, a plane function entity, and a radio unit, the base station operable to communicate as a peer over the radio area network, wherein the low latency unit is operable to receive data from at least one of the plurality of $CO_2$ sensing devices and the plane function entity is operable to receive data from the low latency unit, wherein each of the plurality of $CO_2$ sensing devices is operable to transmit a CO2 measurement to the base station over the radio area network; and a local server configured to process the CO2 measurement, wherein the plane function entity is operable to transmit the CO2 measurement to the local server after receipt from the low latency unit, wherein the local server is configured to determine a CO2 flux measurement using the CO2 measurement.

2. The system of claim 1, comprising a server configured to communicate with a cloud computing service over a network, wherein the plane function entity is operable to transmit the CO2 measurement to the server after receipt from the low latency unit.

3. The system of claim 1, wherein the CO2 sensor comprises a non-dispersive infrared CO2 sensor.

4. The system of claim 1, wherein each $CO_2$ sensing device of the plurality of $CO_2$ sensing devices comprises a battery.

5. A method for monitoring carbon dioxide ($CO_2$) in a subsurface reservoir, comprising:

receiving, at a low latency unit of a base station and over a radio area network, a CO2 measurement from a CO2 sensing device disposed in the subsurface reservoir, the CO2 sensing device comprising a $CO_2$ sensor, a radio unit, and a microprocessor, and the base station comprising a low latency unit, a plane function entity, and a radio unit, the base station operable to communicate as a peer over the radio area network, providing the CO2 measurement from the low latency unit to a plane function entity of the base station; and transmitting the CO2 measurement from the plane function entity of the base station to a server, wherein the server comprises a local server configured to determine a CO2 flux measurement using the CO2 measurement.

6. The method of claim 5, comprising transmitting the CO2 data from the CO2 sensing device disposed in the subsurface reservoir to the base station.

7. The method of claim 5, comprising deploying the CO2 sensing device in the subsurface reservoir via an injection well accessing the subsurface reservoir.

8. The method of claim 5, wherein the server is configured to communicate with a cloud computing service over a network.

9. The method of claim 5, wherein the CO2 sensor comprises a non-dispersive infrared CO2 sensor.

10. The method of claim 5, wherein the CO2 sensor comprises a battery.

11. A non-transitory computer-readable storage medium having executable code stored thereon for monitoring carbon dioxide ($CO_2$) in a subsurface reservoir, the executable code comprising a set of instructions that causes a processor to perform operations comprising:

receiving, at a low latency unit of a base station and over a radio area network, a CO2 measurement from a CO2 sensing device disposed in the subsurface reservoir, the CO2 sensing device comprising a $CO_2$ sensor, a radio unit, and a microprocessor, and the base station comprising a low latency unit, a plane function entity, and a radio unit, the base station operable to communicate as a peer over the radio area network;

providing the CO2 measurement from the low latency unit to a plane function entity of the base station; and transmitting the CO2 measurement from the plane function entity of the base station to a server, wherein the server comprises a local server configured to determine a CO2 flux measurement using the CO2 measurement.

12. The non-transitory computer-readable storage medium of claim 11, the operations comprising transmitting the CO2 data from the CO2 sensing device disposed in the subsurface reservoir to the base station.

13. The non-transitory computer-readable storage medium of claim 11, wherein the server is configured to communicate with a cloud computing service over a network.

14. The non-transitory computer-readable storage medium of claim 11, wherein the CO2 sensor comprises a non-dispersive infrared CO2 sensor.

* * * * *